United States Patent
Monk et al.

(10) Patent No.: US 8,663,973 B2
(45) Date of Patent: Mar. 4, 2014

(54) CONTROLLED ALTERATION OF PORES USING FLUID FLOW AND FABRICATION OF ARTICLES THEREBY

(75) Inventors: David J. Monk, Rexford, NY (US); David R. Walt, Boston, MA (US)

(73) Assignee: Tufts University, Medford, MA (US)

( * ) Notice: Subject to any disclaimer, the term of this patent is extended or adjusted under 35 U.S.C. 154(b) by 1168 days.

(21) Appl. No.: 11/658,515

(22) PCT Filed: Jul. 26, 2005

(86) PCT No.: PCT/US2005/026323
§ 371 (c)(1),
(2), (4) Date: Apr. 10, 2009

(87) PCT Pub. No.: WO2006/025977
PCT Pub. Date: Mar. 9, 2006

(65) Prior Publication Data
US 2009/0215143 A1   Aug. 27, 2009

Related U.S. Application Data

(60) Provisional application No. 60/590,936, filed on Jul. 26, 2004.

(51) Int. Cl.
*B05D 1/36* (2006.01)
*B05D 5/12* (2006.01)
*B05D 7/22* (2006.01)

(52) U.S. Cl.
USPC .......... 435/283.1; 427/532; 427/58; 427/105; 427/123; 427/125; 427/163.2; 427/181; 427/202; 427/203; 427/205; 427/230; 427/299; 427/402

(58) Field of Classification Search
USPC ........ 427/532, 58, 105, 123, 125, 163.2, 181, 427/202, 203, 205, 230, 299, 402; 435/283.1–309.4
See application file for complete search history.

(56) References Cited

U.S. PATENT DOCUMENTS 5,378,343 A * 1/1995 Kounaves et al. ............. 204/413
2004/0045828 A1 * 3/2004 Ratnayake et al. ........... 204/454

OTHER PUBLICATIONS

International Preliminary Report on Patentability for PCT/US2005/026323 issued Jan. 30, 2007, 4 pages.*
Frazier, A.B. et al., "Two Dimensional Metallic Microelectrode Arrays for Extracellular Stimulation and Recording of Neurons," IEEE Proceedings of the Micro Electro Mechanical Systems Conference, 1993, pp. 195-200.*
Frazier, A.B. et al., "Two Dimensional Metallic Microelectrode Arrays for Extracellular Stimulation and Recording of Neurons", IEEE Proceedings of the Micro Electro Mechanical Systems Conference, 1993, pp. 195-200.

* cited by examiner

*Primary Examiner* — William Phillip Fletcher, III
(74) *Attorney, Agent, or Firm* — Fish & Richardson P.C.

(57) ABSTRACT

The invention relates to microscopic structures and methods of making and using the structures. A method of forming a microscopic structure of a material includes obtaining a solution (310) containing the material, establishing a flowing stream of the solution (310) in a capillary (104), wherein the capillary (104) has an inner dimension that is smaller than about 300 micrometers, and maintaining the stream until a layer is built up along an inner wall of the capillary (104) from material deposited from the flowing stream, thereby forming a microscopic structure.

44 Claims, 2 Drawing Sheets

CONTROLLED ALTERATION OF PORES USING FLUID FLOW AND FABRICATION OF ARTICLES THEREBY

CROSS-REFERENCE TO RELATED APPLICATIONS

This application claims priority under 35 U.S.C. §119(e) to U.S. patent application Ser. No. 60/590,936, filed on Jul. 26, 2004, the entire contents of which are hereby incorporated by reference.

TECHNICAL FIELD

This disclosure relates to alteration of pores, and more particularly to the controlled alteration of pores using fluid flow and the fabrication of articles thereby.

BACKGROUND

There is a virtually endless list of applications for devices that can provide stimuli to and/or receive output from and/or detect states of an object or sample, including living organisms, machines, chemicals, biological samples, etc. For example an electrical conductor (e.g., a wire or an electrode) can deliver electrical energy to an object or sample to stimulate the object or sample. Also, an electrical conductor can sense an electrical impulse produced by the object or sample. An optical fiber can deliver light to an object or sample, and can guide light reflected from, transmitted through, or produced by the object or sample to a detector. Bundles of electrical conductors and optical fibers can be used to deliver or receive a multiplicity of electrical and/or optical signals from an object or sample or a multiplicity of objects or samples.

As technology advances, the fabrication and use of ever smaller electrical conductors and optical fibers and higher densities of conductors and fibers has become desirable.

SUMMARY

Techniques are described for altering interior pore surfaces (e.g., capillaries and other regular and irregular shaped voids with constant or varying internal dimensions) of porous substrates using sequential fluid flow of surface altering materials. The invention is based, in part, on the discovery that materials can be grown radially inwardly on the inner walls of a porous substrate's pores, by selectively depositing materials on the substrate walls using controlled reactions (e.g., by self assembly, electrochemical deposition, electroless deposition, in situ polymerization, biological reaction, and/or chemical reaction, hereinafter termed "deposition") under fluid flow, thereby forming structures. Likewise, material may be removed radially outwardly from the surface of the pores of a substrate using controlled reactions (e.g., by dissolution, etching, biological reaction, and/or chemical reaction, hereinafter termed "removal") under fluid flow. The deposition and removal process is achieved using fluid flow to transport materials into pores and to enable the controlled deposition or removal of materials. Using the techniques described herein it is possible to generate complex three-dimensional structures and multiplicities of structures from the macro to nano-scale range.

In a first general aspect, the invention features methods of forming microscopic structures of a material by obtaining a solution containing the material, establishing a flowing stream of the solution in a capillary, wherein the capillary has an inner dimension that is smaller than about 300 micrometers, and maintaining the stream until a layer is built up along an inner wall of the capillary from material deposited from the flowing stream, thereby forming a microscopic structure.

The methods can include one or more of the following features. For example, the inner dimension can be smaller than about 100 microns, smaller than about 30 microns, smaller than about 10 microns, smaller than about 3 microns, smaller than about 1 micron, smaller than about 300 nanometers, smaller than about 100 nanometers, smaller than about 30 nanometers, or smaller than about 10 nanometers. The capillary can have a length of at least 10 microns, of at least 100 microns, of at least 1 millimeter, of at least 1 centimeter, of at least 10 centimeters, of at least 1 meter, or of at least 10 meters.

The methods can further include depositing a bonding layer on the inner wall of the capillaries onto which material from the flowing stream is deposited. The bonding layer can include a bifunctional linker that binds to the inner wall of the capillary at a first end and that binds to material contained in the flowing stream at a second end, and the bonding layer can include silane, or (3-aminopropyl)-trimethoxysilane). Depositing the bonding layer can include establishing a flowing stream of a solution containing a material that is deposited onto the inner walls of the capillaries to form the bonding layer and maintaining the stream until the bonding layer is built up along an inner wall of the capillaries.

The methods can further include, before establishing the flowing stream of solution within the capillaries, establishing a flowing stream of a solution containing a colloidal suspension of particles within the capillaries and maintaining the flowing stream of the colloidal suspension of particles until a layer of particles is built up on the bonding layer, such that material deposited from the flowing stream is deposited onto the layer of particles. The flowing stream of solution can include a substance that reacts with the layer of particles to deposit material onto the layer of particles. The colloidal suspension of particles can include gold colloid particles, silver colloid particles, palladium colloid particles, platinum colloid particles, tin colloid particles, and/or palladium/tin colloid particles.

The microscopic structures can be electrically conductive. In various implementations, the material deposited from the flowing stream can be a metal, for example, gold, silver, copper, nickel, tin, cobalt, platinum, or palladium. The capillary can be formed within a hollow optical fiber.

The methods can further include establishing a flowing stream of the solution in an assembly of capillaries, wherein each capillary has an inner dimension that is smaller than about 300 micrometers, and maintaining the stream until a layer is built up along an inner wall of the capillaries from material deposited from the flowing stream, thereby forming a plurality of microscopic structures. In certain implementations, the assembly of capillaries can be arranged in an array structure.

In another general aspect, the invention includes an apparatus produced by the new methods, or any of its implementations.

The apparatuses can include a capillary, wherein the capillary has an inner dimension that is smaller than about 300 micrometers, and an electrically conductive microelectrode formed within the capillary, wherein the microelectrode has a long dimension and a short dimension and the ratio between the long dimension and the short dimension is greater than about 500.

The apparatuses can include one or more of the following features. For example, the short dimension can be a diameter.

The ratio of the length to the width or diameter can be greater than about 1000, or greater than about 3000.

The apparatuses can further include an assembly of capillaries, where each of the capillaries has an inner dimension that is smaller than about 300 micrometers, where an electrically conductive microelectrode is formed within each of the capillaries, and where the microelectrodes have a long dimension and a short dimension, and the ratio between the long dimension and the short dimension is greater than about 500, 1000, or 3000.

The assembly of capillaries can be arranged in an array structure. Each capillary of the assembly can be formed within a distinct optical fiber. Each microelectrode of the assembly can be individually electrically addressable, and the optical fibers can be individually optically addressable.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

Techniques are provided for the creation of structures, assemblies of structures, and arrays of structures in a highly-controlled manner through selective growth or removal of material within capillaries or pores of a substrate. As used herein, disordered groupings of two or more individual structures are referred to as "assemblies," and ordered groupings of two or more individual structures are referred to as "arrays." The deposition of material on a substrate and removal of material from a substrate is achieved through controlled reactions that result in the formation of structures having macro- to nano-scale dimensions. Such structures can have a very high aspect ratio between the longest and the shortest dimensions of the structure. Structures fabricated on the substrate can be freed from the substrate by selective removal of the substrate material.

A porous substrate can be subjected to one or more fluid flows containing one or more reagent materials. Materials or products of reactions between materials contained in one or more of the flows can react with or become bound to the surface of the pore walls of the substrate. The resulting bound material that coats the substrate's pore walls (e.g., a crosslinker, reactant, catalyst, or biological material that bonds to the substrate) can form a layer or layers on the inside walls of the porous substrate and may be chosen to be catalytic (i.e., it will bond to, react with, or enable the growth of another material upon it). The substrate pores coated with one or more catalytic layers of material and can be subjected to a subsequent solution or solutions of one or more components that are reactive or catalytic, which in turn deposit an additional layer or layers on the substrate's pore walls, such that material builds up on the inside walls of the substrate pores. After extended sequences or longer times, the thickness of the deposited material can approach the physical dimensions of the pore space. Similarly, the porous substrate may be subjected to fluid flows containing one or more reagent materials such that materials or a product of the reaction between materials in the flows reacts with or removes materials from the porous substrate wall.

The use of fluid flow to grow structures allows precise control of growth conditions (e.g., deposition length, initiation, and termination of the deposition). Because multiple pores of a substrate can be subjected to simultaneous solution flow, one reagent stream can feed many individual pores arranged in a parallel configuration or in a branched structure with a main trunk and subsequent branches. When many pores are arranged in an assembly or array structure, many structures can be created simultaneously to create an assembly or array of structures.

A general technique for fabricating structures within pores of a substrate is as follows. A clean porous substrate containing, for example, regularly or irregularly shaped capillaries, tubes, cylinders, and/or other regular or irregular shaped voids with constant or varying internal dimensions is subjected to fluid flow, which can be driven by pressure, electroosmosis, etc. in a continuous or pulsed manner. The fluid flowing through the substrate pores can contain one or more materials (e.g., a crosslinker, reactant, catalyst, biological material, or other deposition material) that bond to the inside surface of the pores of the substrate. Material contained in the fluid flow can be deposited on the walls of the substrate to fabricate structures in several ways. For example, during single-step fabrication, material contained in the fluid flow is deposited on the substrate walls to form a layer of material. During multi-step fabrication, a layer of reactive or catalytic material is deposited on the substrate walls, which facilitates the deposition of a layer of second material on the layer of the catalytic material. The second material can be deposited in a continuous fashion that is sufficient for the desired application, or the second material can behave as a catalyst for the deposition of a layer of a third material that is sufficient for the desired application. In particular, during a multi-step fabrication of a metal structure within a silica capillary, the first material deposited can be silane because it has an affinity for silica and electrically conductive metal colloid, and the second material deposited can be an electrically conductive metal colloid. This technique facilitates the deposition of bulk electrically conductive metal on the surface of silica substrate walls. In a single-step fabrication, the substrate walls themselves can possess sufficient catalytic properties to facilitate direct deposition of an electrically conductive material on the substrate walls. The fabrication techniques are described in more detail below with reference to several examples.

Porous Light-Guiding Substrates

Figure 1:
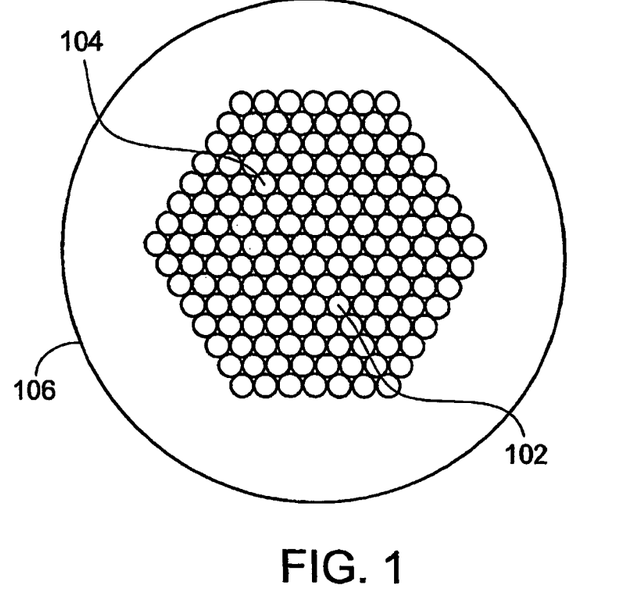
FIG. 1 is a schematic end view of an array of optical fiber capillaries.

FIG. 1 shows a porous substrate 100 capable of guiding light. The substrate 100 can include a bundle 102 of capillaries (e.g., hollow optical fibers) arranged in a hexagonally closest packed array 104 within the center of a silica rod 106. All optical fibers within the array 104 have approximately the same diameter, so that they can be arranged in a periodic array of fibers. The diameters of the capillaries can be, for example, smaller than about 300 microns, about 100 microns, about 30 microns, about 10 microns, about 3 microns, about 1 micron, about 300 nm, or about 100 nm.

Figure 2:
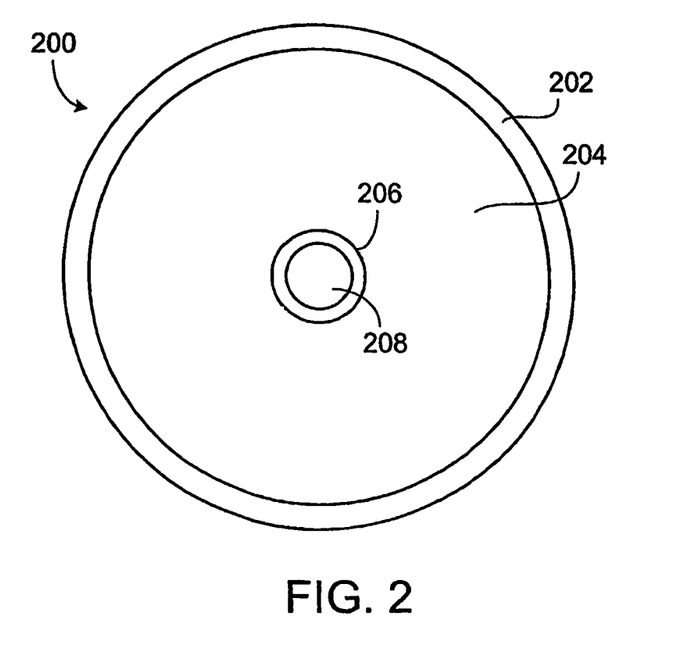
FIG. 2 is a schematic end view of one optical fiber capillary of the array shown in FIG. 1.

As shown in FIG. 2, an optical fiber 200 of the bundle 102 is made of a series of concentric rings of materials. The outside optical fiber cladding 202 can be an optically transparent material having a refractive index, $n_1$. The optical fiber core material 204 can be an optically transparent material having a refractive index, $n_2$. The inside optical fiber cladding 206 can be an optically transparent material having a refractive index, $n_3$. The center of each optical fiber has a hollow core that forms a capillary extending through the entire rod 106. Light can be conducted from one end of the fiber 200 to the other in the core provided the refractive index of the core, $n_2$, is greater than the refractive indices of the cladding materials, $n_1$ and $n_3$. Light can be conducted from one end of the fiber to the other in the capillary when the core has a refractive index greater than that of the cladding, $n_3$, or provided the walls of the hollow core are coated with an optically reflective material (e.g., gold, silver, or other metallic or non-metallic materials). Capillary arrays used in the examples described below can be purchased from Collimated Holes Incorporated (Campbell, Calif.). They were fabricated using a drawing technique used to prepare a rod 106 with a circular outside diameter of 2 mm and an array 104 of 631 optical fibers each having outer diameters of about 40 μm and capillary diameters of about 10 μm.

Flowing Liquids Through the Porous Substrate

The circumference of the rod 106 containing an optical fiber capillary array 104 was etched with a diamond scribe or capillary cutter and broken into approximately 5 cm lengths. Capillaries can be various lengths, e.g., they can be longer than about 1 mm, about 3, mm, about 1 cm, about 3 cm, about 10 cm, about 30 cm, about 1 m, about 3 m, or about 10 m. Instead of creating capillaries in optical fibers, an assembly or array of capillaries can also be produced in a thin film or membrane of material. For example, multiple capillaries can be etched in silica or semiconductor film. Thus, capillaries can also have a length of less than about 3 mm, about 1 mm, about 300 microns, about 100 microns, about 30 microns, about 10 microns, about 3 microns, or about 1 micron.

Figure 3:
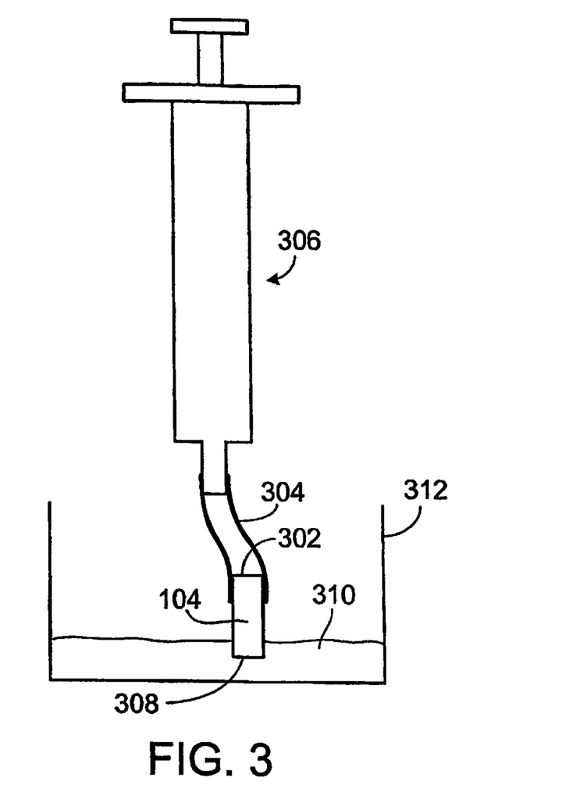
FIG. 3 is a schematic view of an arrangement for drawing a solution through the array shown in FIG. 1.

As shown in FIG. 3, one end 302 of the array 104 was fitted inside a short length of flexible tubing (e.g., Tygon® tubing) or another suitable flangeless high pressure fitting that was attached to a syringe 306. The syringe 306 was used in conjunction with a syringe pump to create positive or negative pressure sufficient to flow a solution through the capillary array 104. The pressure is chosen to cause fluid to flow though the capillaries at a desired flow rate and can range from a fraction of a psi to about 10,000 psi. Other pumps and plumbing techniques can also be used to enable higher flow rate, pressures, etc. For example, a second end 308 of the rod 106 containing the capillary array 104 can be immersed in a solution 310 within a beaker 312. The solution 310 can contain material to be deposited on the substrate walls of the capillary array 104, and the solution 310 can be drawn through the capillaries of the array 104 by creating a negative pressure in the syringe 306. Alternatively, the syringe 306 can be filled with solution 310, and the solution 310 can be pushed through the capillaries of the array 104 by creating a positive pressure on the syringe 306. The positive pressure (ΔP) required to flow materials through the capillaries may be estimated by inputting the viscosity (η) of the solution to be flowed through the pore, the desired volumetric flow rate (F), the radius of the capillary (r), and the length of the capillary (L) into Poiseuille's equation for laminar flow in a small diameter capillary:

$$F = \frac{(\Delta P * \pi * r^4)}{(8 * \eta * L)}$$

Cleaning the Pores of the Porous Substrate

To clean the substrate walls of the optical fiber capillary array 104 and leave the surfaces completely protonated or deprotonated prior to deposition of materials within the solution 310, a small volume of 1 M sodium hydroxide or other strong base, 1 M sulfuric acid or other strong acid, aqua regia (3:1 nitric acid: hydrochloric acid), or piranha solution (3:1 concentrated sulfuric acid: 30% hydrogen peroxide) can be drawn into or flowed through the capillaries for one minute or longer. Although strong bases are effective for cleaning, they are not used on all surfaces because they can etch the surface of some substrates. The capillaries are rinsed by flowing an aliquot of water through them, followed by an aliquot of alcohol, e.g., methanol, ethanol, or isopropanol to remove residual water.

Deposition of Catalytic Material Within Pores of the Substrate

After the inner walls of the optical fiber capillaries in the array 104 have been cleaned, the cleaned inner walls are subjected to formation of one or more monolayers of a catalytic material. In the case of colloidal gold deposition on a silica substrate, a small volume of 1 to 10% by volume of silane (e.g., (3-aminopropyl)-trimethoxysilane) in a suitable solvent (e.g. methanol) is drawn into or pumped through the capillaries. This chemical acts as a primary catalytic material because it has an affinity for both the substrate and secondary deposition material and readily forms a covalent bond with the substrate surface. For example, to facilitate the deposition of gold within pores of a silica substrate, a solution containing (3-aminopropyl)-trimethoxysilane can be passed through pores of the silica substrate, because the triethoxysilane group has an affinity for silica, and the amine group has an affinity for gold. Thus, the trimethoxysilane group bonds to remaining surface hydroxyl groups on the inner silica surface of the substrate's capillary walls, leaving a homogenous surface monolayer of aminopropyl tails that face towards the center of the capillaries. The capillaries are allowed to silanize for approximately 3-8 hours at room temperature to allow at least a monolayer of silane to form on the silica surfaces. After silanization of the silica substrate surfaces, the capillaries are flushed with an aliquot of methanol followed by and aliquot of water to remove residual (3-aminopropyl)-trimethoxysilane bifunctional linking material from the capillaries.

Other bifunctional linking materials can also be used to facilitate the growth of material layers on the walls of a substrate. For example, for growing a gold layer on glass (2-cyanoethyl)triethoxysilane can be used as the bifunctional linker. For growing a layer of colloidal gold on glass, poly (diallyldimethylammonium chloride) can be used as the bifunctional linker, as can be the following silanes: (3-mercaptoproply)trimethoxysilane; (mercaptomethyl)dimethylethoxysilane; (mercaptomethyl)methyldiethoxysilane; (3-aminopropyl)trimethoxysilane; (3-aminopropyl)methyldiethoxysilane; (3-cyanopropyl)dimethylmethoxysilane; (3-cyanoproply)triethoxysilane; (2-pyridylethyl)trimethoxysilane; and (2-(diphenylphosphino)ethyl)triethoxysilane. For growing a layer of colloidal Pd/Sn on a glass substrate, 3-(2-aminoethylamino)-propyl-trimethoxysilane can be used as the bifunctional linker, and for growing a layer of colloidal gold on an $Al_2O_3$ substrate, (3-mercaptoproply)methyldimethoxysilane can be used. For growing a layer of poly (aniline) on a glass substrate adipoyl chloride and p-phenylenediamine can be used as the bifunctional linking material.

Deposition of Colloidal Materials Within the Pores of the Substrate

Various colloidal materials can be deposited within pores of the substrate wising the techniques described herein. One example, in which colloidal gold is deposited is described below. Other materials can be deposited in a similar fashion.

Following deposition of the bifunctional liking material (e.g., (3-aminopropyl)-trimethoxysilane) on the surfaces of the substrate, a solution of colloidal gold is flowed through the capillaries by using a new syringe to provide the pressure to create a flow of solution of suspended gold particles through the capillaries. The colloidal gold is attracted to the amine functionality and forms a monolayer of the colloid inside the capillaries. The immobilized colloidal gold is used as a seed to chemically deposit a bulk conductive hollow microwire.

A colloidal gold solution is prepared according to standard techniques. All glassware and stir bars used for colloidal gold preparation are washed with freshly prepared 3:1 hydrochloric acid:nitric acid (also known as "aqua regia"). A solution of hydrogen tetrachloroaurate (III) trihydrate (0.0401 g dissolved in 100 mL water) is prepared and added to a 500 mL round bottom flask with a magnetic stir bar for continuous mechanical stirring. A condenser is attached, and the pale yellow solution is brought to a boil. An aqueous solution of sodium citrate tribasic dihydrate (0.06 g in 5 mL) is added, and the solution is refluxed for 10 minutes. The resulting purple suspension is removed from the heat, cooled to room temperature, and transferred to an amber bottle for storage at 4° C. When the colloidal gold is examined with the UV-visible spectrum, it exhibits a strong surface plasmon band at 527 nm.

An aliquot of the suspension of colloidal gold is filtered though a 0.45 μm filter and drawn through the capillaries by a syringe 306, as shown in FIG. 3. Alternatively, the colloidal gold suspension can be injected from the syringe 306 through the capillary array 104. Before the colloidal gold solution is flowed through the capillaries, the capillaries are transparent. As the purple colloidal gold suspension begins to flow through the capillaries a blue color becomes visible at the input end of the capillaries, however, the liquid flowing out from the end of the array 104 is clear. As the suspension continues to flow through the capillaries and available binding sites for colloidal gold become occupied, the blue color migrates along the length of the capillaries, and the liquid flowing out of the array becomes a purple color, because it contains an increasing amount of unbound colloidal gold. By the end of the process when most of the binding sites have been occupied, the capillaries become a uniform deep blue color, and the effluent flow is similar in color to the original solution. Total deposition time is a few minutes.

Growth of Microtubes and Microwires Within the Substrate Pores

After a layer of catalyst material is formed within the capillaries, a gold layer is grown and thickened by an electroless gold plating technique. The electroless plating solution is made immediately prior to use by mixing 1:10 4 mM hydroxylamine hydrochloride: 0.01% hydrogen tetrachloroaurate(III) trihydrate. This solution is drawn through the capillaries by a syringe 306. The reduction of gold(III) to elemental gold(0) by hydroxylamine hydrochloride is greatly catalyzed at the surface of elemental gold. Hence, elemental gold is deposited on the surface of the immobilized colloidal gold, increasing the thickness of the gold layer until a bulk conductive layer is formed. The gold layer grows radially inwardly on the inner cylindrical surface within the capillaries as the gold-containing solution flows through the capillaries and delivers gold in solution to the cylindrical growth surface. As the solution flows through the capillary and the wall thickness of the gold tubes increases, the color of the capillary, as viewed from the exterior, changes from blue to reflective gold. Solution can be flowed through the capillary tubes until a desired thickness of the gold microtubes walls is achieved. Eventually, the wall thickness of the hollow gold microtubes approaches the radius of the pore.

Radially growing microtubes and microwires can be contrasted with other growth methods. For example, a wire could be grown axially within a capillary having a circular gold surface that seals one end of the capillary by filling the capillary with a gold solution and allowing the gold to diffuse to the circular growth surface. However, for a capillary open at both ends having a length, L, and a radius, r, the surface area on which the gold layer can grow radially is $2\pi L$. For a high-aspect ratio capillary (i.e., in which L>>r), this surface area is much greater than the surface area upon which a microwire can be grown axially in a capillary closed at one end (i.e., $\pi^2$). Furthermore, gold is delivered to the growth surface by flowing a fluid stream of molecules containing gold atoms over the growth surface, rather than by the diffusion of molecules with a stagnant fluid.

Thus, flowing gold and growing a conductive layer in a radial direction can produce microtubes and microwires with macroscopic to sub-micrometer diameters and very high aspect ratios in a short amount of time. Because the gold material in solution is delivered to the growth surface by the flowing stream of solution rather than by diffusion, the growth rate of individual structures is primarily limited by Poiseuille's equation for laminar flow in a straight pipe:

$$F = \frac{(\Delta P * \pi * r^4)}{(8 * \eta * L)}$$

where F is the flow rate, $\Delta P$ is the change in pressure across the pipe, $\eta$ is the viscosity of the fluid, r is the radius of the pipe, and L is the length of the pipe. It should be noted that the minimum diameter, maximum length, and deposition uniformity are also limited by the decrease in reagent concentration across the length of the capillary, which, in turn, can depend on the flow rate of fluid through the pores and surface chemistry of the deposited materials with the walls of the pores The wall thickness uniformity of the grown microtubes can be enhanced and occlusion at the orifice of the capillary can be reduced by filtering solutions containing materials to be deposited prior to use to remove particulates for the solutions, which allows the formation of long wires within the capillaries.

Growth of Gold Microtubes Through Sequential Deposition of Crosslinking Material and Colloidal Gold Gold microstructures can also be grown sequentially by depositing layers of bifunctional linking materials and colloidal gold.

The array 104 is prepared for deposition of a bifunctional linker on the walls of the capillaries by cleaning the surface walls. After the inner walls of the capillaries in the array 104 have been cleaned, the cleaned inner walls are subjected to formation of a monolayer of bifunctional chemical.

For example, in the case of colloidal gold deposition on a silica substrate, a small volume of 1 to 10% by volume of silane (e.g., (3-aminopropyl)-trimethoxysilane) in a suitable solvent (e.g., methanol) can be drawn into or pumped through the capillaries. The bifunctional chemical has an affinity for both the substrate and the catalyst material and readily forms a covalent bond with the substrate surface. For example, in the case of (3-aminopropyl)-trimethoxysilane with the silica arrays specified above, the triethoxysilane group has an affinity for silica and the amine group has an affinity for gold. Thus, the trimethoxysilane group bonds to remaining surface hydroxyl groups on the inner silica surface of the capillary walls, leaving a homogenous surface monolayer of amine tails that face towards the center of the capillaries. The capillaries are allowed to silanize for about 3-8 hours at room temperature. After silanization, the capillaries are flushed with an aliquot of methanol followed by an aliquot of water by flowing these materials through the capillaries.

Following silanization of the surface walls, a solution of colloidal gold is flowed through the capillaries using a new syringe to provide the pressure to create a flow of solution of suspended gold particles through the capillaries. A colloidal gold solution is prepared according to standard techniques. All glassware and stir bars used for colloidal gold preparation are washed with freshly prepared aqua regia. A solution of hydrogen tetrachloroaurate (III) trihydrate (0.0401 g dissolved in 100 mL water) is prepared and added to a 500 mL round bottom flask with a magnetic stir bar for continuous mechanical stirring. A condenser is attached, and the pale yellow solution is brought to a boil. An aqueous solution of sodium citrate tribasic dihydrate (0.06 g in 5 mL) is added, and the solution is refluxed for 10 minutes. The resulting purple suspension is removed from the heat, cooled to room temperature, and transferred to an amber bottle for storage at 4° C. When the colloidal gold is examined with the UV-visible spectrum, it exhibits a strong surface plasmon band at 527 nm.

The suspension of colloidal gold is filtered though a 0.45 μm filter and drawn through the capillaries with a syringe 306, as shown in FIG. 3. Alternatively, the colloidal gold suspension can be injected from the syringe 306 through the capillary array 104. Before the colloidal gold solution is drawn through the capillaries, the capillaries are transparent. As the purple colloidal gold suspension begins to flow through the capillaries, a blue color becomes visible at the input end of the capillaries, however, the liquid flowing out from the end of the array 104 is clear. As the suspension continues to flow through the capillaries and available binding sites for colloidal gold become occupied, the blue color migrates along the length of the capillaries, and the liquid flowing out of the array becomes a purple color, because it contains an increasing amount of unbound colloidal gold. By the end of the process, when most of the binding sites for have been occupied, the capillaries become a uniform deep blue color, and the effluent flow is similar in color to the original solution. The total deposition time is a few minutes. After this step, the capillaries are flushed with an aliquot of water followed by an aliquot of methanol.

After a layer of colloidal gold is formed within the capillaries, the gold layer is grown and thickened by repetitive deposition of layers of crosslinking material and colloidal gold. A crosslinking solution of 2-mercaptoethylamine in methanol is flowed through the array, and the sulfur and amine functionalities bind to the colloidal gold, leaving a surface layer of amine and sulfur tails that face towards the center of the capillary tubes. Total deposition time is a few minutes. After deposition of the 2-mercaptoethylamine layer, the capillaries are flushed with an aliquot of methanol followed by an aliquot of water. This provides an additional layer for colloidal gold binding. The colloidal gold deposition step and the 2-mercaptoethylamine deposition can be repeated multiple times to form sequential layers of colloidal gold and 2-mercaptoethylamine on the surface of the immobilized colloidal gold, increasing the thickness of the colloidal gold layer until a bulk conductive layer is formed. The colloidal gold layers grow radially inwardly on the inner cylindrical substrate surfaces within the capillaries as the alternating 2-mercaptoethylamine and colloidal gold-containing solutions flow through the capillaries. As the process is repeated, the alternating solutions can be flowed through the capillary tubes until a desired thickness of the colloidal gold microtubes is achieved. Eventually, the wall thickness of the hollow microtubes approach the shape of solid wires. The colloidal layers may be sintered into an electrically continuous layer by applying sufficient heat to the substrate.

Growth of Conductive Structures Within Substrate Pores by a Single-Step Deposition The capillary or capillary array 104 is prepared for deposition of a conductive metal (e.g., silver) on the walls of the capillaries. After the inner walls of the capillaries in the array 104 have been cleaned, the cleaned inner walls of are subjected to formation of a layer of silver.

First, three solutions are prepared: (a) 0.147 M silver nitrate in water; (b) 0.8 M potassium hydroxide in water; and (c) 800 ml 0.234 M sucrose with 100 mL ethanol and 3.5 mL nitric acid. The three solutions are mixed in a ratio of a:b:c=16:8:1, but prior to mixing, concentrated ammonium hydroxide is added to the aliquot of solution (a) until a precipitate forms and just disappears. The aliquot of solution (b) is added to the solution (a), and a dark-brown or black precipitate is formed. Concentrated ammonium hydroxide is added dropwise until the precipitate almost completely dissolves, however, some precipitate should remain. Then, the aliquot of solution (c) is added, and the combined solution is then mixed and filtered through a 0.45 μm filter.

The filtered solution is drawn through the capillary array 104 using a syringe 306, as shown in FIG. 3. Alternatively, the silver plating solution can be injected from the syringe 306 through the capillary array 104. Before the silver solution is drawn through the capillaries, the capillaries are transparent, but as the silver plating solution begins to flow through the capillaries, a brownish silver color becomes visible in the capillaries. As the solution continues to flow through the capillaries, the color deepens along the length of the capillaries. By the end of the process, the capillaries become a uniform, metallic silver color, similar to a mirror. Total deposition time is a few minutes.

After the initial layer of silver is formed within the capillaries, the silver layer may be grown and thickened by continued flow of the silver plating solution through the capillaries. Hence, elemental silver is deposited on the surface of the bound silver, increasing the thickness of the silver layer until a bulk conductive layer is formed. The silver layer grows radially inwardly on the inner cylindrical surface within the capillaries as the silver plating solution flows through the capillaries and delivers silver in solution to the cylindrical growth surface. As the solution flows through the capillary and the wall thickness of the silver tubes increases, the color of the capillary, as viewed from the exterior, changes to reflective silver. Silver plating solution can be flowed through the capillary tubes until a desired thickness of the silver microtubes walls is achieved. Eventually, hollow microtubes become solid wires.

Additionally, the silver surface may be used for electroless deposition of other metals, for example gold. In this case, the electroless plating solution is made immediately prior to use by mixing either a solution containing 1:10 4 mM hydroxylamine hydrochloride: 0.01% hydrogen tetrachloroaurate(III) trihydrate, or a solution containing $7.9 \times 10^{-3}$ M $Na_3Au(SO_3)_2$, 0.127 M sodium sulfite, and 0.625 M formaldehyde. The pH of this solution may be adjusted by adding sodium bicarbonate followed by dilute sulfuric acid, because lower pH results in a slower deposition rate of material on the substrate walls. Either of these solutions can be drawn through the capillaries, e.g., by a syringe 306.

Alternatively, the plating solution can be injected from the syringe 306 through the capillary array 104. The reduction of gold(III) or gold(I) to elemental gold(0) by hydroxylamine hydrochloride or formaldehyde is greatly catalyzed at the surface of elemental silver or elemental gold. Elemental gold is deposited on the surface of the silver, increasing the thickness of the gold layer until a bulk conductive layer is formed. The gold layer grows radially inwardly on the inner cylindrical surface within the capillaries as the gold-containing solution flows through the capillaries and delivers gold in solution to the cylindrical growth surface. As the solution flows through the capillary and the wall thickness of the gold tubes increases, the color of the capillary, as viewed from the exterior, changes from silver to reflective gold. Solution can be flowed through the capillary tubes until a desired thickness of the gold microtubes walls is achieved. Eventually, the wall thickness of the hollow microtubes approach the shape of solid wires.

Growth of Silver Structures Within the Substrate Pores by a Two-Step Process

The capillary or capillary array 104 is prepared for deposition of a layer of tin(II) chloride on the walls of the capillaries. After the inner walls of the capillaries in the array 104 have been cleaned, the cleaned inner walls are subjected to formation of a layer of tin(II) chloride by the following process.

The following two solutions are prepared: 0.026 M tin(II) chloride and 0.07 M trifluoroacetic acid in water; and 0.029 M ammoniacal silver nitrate in water. The solutions are filtered through a 0.45 μm filter prior to use.

First, the filtered solution of tin(II) chloride/trifluoroacetic acid is drawn through the capillary array with the syringe 306, as shown in FIG. 3, using the techniques described above. Alternatively, the tin(II) chloride/trifluoroaceticacid solution can be injected from the syringe 306 through the capillary array 104. As, the tin(II) chloride/trifluoroacetic acid solution is drawn through the capillaries, and the capillaries remain transparent, and the solution is allowed to flow through the capillaries for approximately 10 minutes. Longer times deposit more tin(II) chloride on the surface of the capillary. After this step, the capillaries are flushed with an aliquot of water.

Next, the filtered ammoniacal silver nitrate solution is drawn through the capillaries. Initially, the capillaries are transparent, but as the ammoniacal silver nitrate solution begins to flow through the capillaries, a brownish silver color becomes visible in the capillaries. As the solution continues to flow through the capillaries, the brownish silver color deepens along the length of the capillaries. By the end of the process, the capillaries become a uniform, brownish silver color. Total deposition time is a few minutes. Longer deposition times deposit more silver on the surface of the capillary. After this step the capillaries are flushed with an aliquot of water.

After the initial layer of silver is formed within the capillaries, the silver layer may be grown and thickened by continued flow of the silver plating solution through the capillaries to deposit elemental silver on the surface of the bound silver and increase the thickness of the silver layer until a bulk conductive layer is formed. The silver layer grows radially inwardly on the inner cylindrical surface within the capillaries as the silver plating solution flows through the capillaries and delivers silver in solution to the cylindrical growth surface. As the solution flows through the capillary and the wall thickness of the silver tubes increases, the color of the capillary, as viewed from the exterior, changes to reflective silver. Silver plating solution can be flowed through the capillary tubes until a desired thickness of the silver microtubes walls is achieved. Eventually, hollow microtubes become solid wires.

Additionally, the silver surface may be used for electroless deposition of other metals, for example gold. In this case, the electroless plating solution is made immediately prior to use by mixing either a solution containing 1:10 4 mM hydroxylamine hydrochloride: 0.01% hydrogen tetrachloroaurate(III) trihydrate, or a solution containing $7.9 \times 10^{-3}$ M $Na_3Au(SO_3)_2$, 0.127 M sodium sulfite, and 0.625 M formaldehyde. The pH of this solution may be adjusted by adding sodium bicarbonate followed by dilute sulfuric acid because lower pH results in a slower deposition rates. Either of these solutions is drawn through the capillaries by a syringe 306. Alternatively, the plating solution can be injected from the syringe 306 through the capillary array 104. The reduction of gold(III) or gold(I) to elemental gold(0) by hydroxylamine hydrochloride or formaldehyde is greatly catalyzed at the surface of elemental silver or elemental gold. Elemental gold is deposited on the surface of the silver, increasing the thickness of the gold layer until a bulk conductive layer is formed. The gold layer grows radially inwardly on the inner cylindrical surface within the capillaries as the gold-containing solution flows through the capillaries and delivers gold in solution to the cylindrical growth surface. As the solution flows through the capillary and the wall thickness of the gold tubes increases, the color of the capillary, as viewed from the exterior, changes from silver to reflective gold. Solution can be flowed through the capillary tubes until a desired thickness of the gold microtubes walls is achieved. Eventually, the wall thickness of the hollow microtubes approach the shape of solid wires.

Growth of Copper, Nickel, Cobalt, and Other Metal Microtubes Within the Substrate Pores by a Two-Step Process Copper, nickel, cobalt, and other metal microstructures also can be grown by sequentially depositing layers of bifunctional linking materials and colloidal palladium or palladium/tin followed by electroless deposition of copper, nickel, cobalt, or other metals.

The array 104 can be prepared for deposition of a bifunctional linker on the walls of the capillaries by cleaning the surface walls. After the inner walls of the capillaries in the array 104 have been cleaned, the cleaned inner walls of are subjected to formation of a monolayer of bifunctional chemical.

For example, in the case of colloidal palladium or colloidal palladium/tin deposition on a silica substrate, a small volume of 1 to 10% by volume of silane (e.g., (3-aminopropyl)-trimethoxysilane) in a suitable solvent (e.g., heptane) can be drawn into or pumped through the capillaries. The silane is a bifunctional chemical that has an affinity for both the substrate and the catalyst material, and it readily forms a covalent bond with the substrate surface. For example, in the case of (3-aminopropyl)-trimethoxysilane with the silica arrays specified above, the triethoxysilane group has an affinity for silica and the amine group has an affinity for palladium. Thus, the trimethoxysilane group bonds to remaining surface hydroxyl groups on the inner silica surface of the capillary walls, leaving a homogenous surface monolayer of amine tails that face towards the center of the capillaries. The capillaries are allowed to silanize for about 3-8 hours at room temperature. After silanization, the capillaries are flushed with an aliquot of heptane followed by and aliquot of toluene by flowing these materials through the capillaries.

Following silanization of the surface walls, a solution of colloidal palladium or colloidal palladium/tin is flowed through the capillaries using a new syringe to provide sufficient pressure to create a flow of solution of suspended palladium or palladium/tin particles through the capillaries.

A colloidal palladium solution can be prepared according to standard techniques. All glassware and stir bars used for colloidal palladium preparation are washed with freshly prepared aqua regia. A suspension of palladium (II) acetate (4 g) and tetraoctadecylammonium bromide (5 g) in 200 mL of 5:1 tolune:THF can be prepared at room temperature and added to a 500 mL round bottom flask with a magnetic stir bar for continuous mechanical stirring. Absolute ethanol (25 mL) is added, a condenser is attached, and the suspension is brought to reflux for about 12 hours, and the color of the solution becomes a cloudy brownish-black. Absolute ethanol (100 mL) is added with vigorous stirring, and the solution is allowed to sit for 5 hours at room temperature. The resulting precipitate is removed from the flask, dried under vacuum, transferred to an amber bottle containing 700 mL toluene, and resuspended using sonication prior to use.

Alternatively, a colloidal palladium/tin solution can be prepared according to standard techniques. All glassware and stir bars used for colloidal palladium/tin preparation is washed with freshly prepared aqua regia. A solution of palladium (II) chloride (0.5 g) in 300 mL water and 150 ml concentrated hydrochloric acid is prepared at room temperature and added to a 500 mL round bottom flask with a magnetic stir bar for continuous mechanical stirring. Tin (II) chloride (25 g) is added and the solution is mixed, and the color of the solution becomes a cloudy brownish-black. The resulting colloid is used immediately.

The suspension of colloidal palladium or colloidal palladium/tin is filtered though a 0.45 µm filter and drawn through the capillaries with a syringe 306, as shown in FIG. 3. Alternatively, the colloidal palladium or colloidal palladium/tin suspension can be injected from the syringe 306 through the capillary array 104. The total deposition time was a few minutes. After this step, the capillaries were flushed with an aliquot of toluene and dried. Tin can be chemically removed from colloidal palladium/tin by flowing 10% perchloric acid or 5% sodium hydroxide through the capillaries to accelerate metal deposition.

After a layer of colloidal palladium or colloidal palladium/tin is formed within the capillaries, a copper layer can be grown using electroless deposition. Two solutions are prepared as follows: solution 1 includes 3 g copper sulfate, 14 g sodium potassium tartrate, and 4 g sodium hydroxide in distilled water (100 mL); and solution 2 includes aqueous formaldehyde (37% by weight). Immediately prior to use, solutions 1 and 2 are mixed in a 10:1 ratio.

After the initial layer of copper is formed within the capillaries, the copper layer can be grown and thickened by continued flow of the copper plating solution through the capillaries to deposit elemental copper on the surface of the bound copper and to increase the thickness of the copper layer until a bulk conductive layer is formed. The copper layer grows radially inwardly on the inner cylindrical surface within the capillaries as the copper plating solution flows through the capillaries and delivers copper in solution to the cylindrical growth surface. As the solution flows through the capillary and the wall thickness of the copper tubes increases, the color of the capillary, as viewed from the exterior, changes to reflective copper. Copper plating solution can be flowed through the capillary tubes until a desired thickness of the copper microtubes walls is achieved. Eventually, hollow microtubes become solid wires.

Additionally, the palladium colloid or colloidal palladium/tin surface may be used for electroless deposition of other metals, for example nickel or cobalt. In the case of nickel, the electroless plating solution is made immediately prior to use by mixing a solution containing nickel (II) chloride (29.8 g), sodium hypophosphite (9.7 g), and sodium (III) citrate (9.7 g) in water (1 L). In the case of cobalt, the electroless plating solution is made immediately prior to use by mixing a solution containing cobalt (II) chloride (29.8 g), sodium hypophosphite (9.7 g), and sodium (III) citrate (9.7 g) in water (1 L). Either of these solutions is drawn through the capillaries at elevated temperature (92° C.) by a syringe 306. Alternatively, the plating solution can be injected from the syringe 306 through the capillary array 104. The reduction of nickel (II) or cobalt (II) to elemental copper or cobalt is greatly catalyzed at the surface of colloidal palladium or colloidal palladium/tin and at elemental nickel or cobalt respectively. Elemental nickel or cobalt is deposited on the surface of the colloidal palladium or colloidal palladium/tin, increasing the thickness of the nickel or cobalt layer until a bulk conductive layer is formed. The nickel or cobalt layer grows radially inwardly on the inner cylindrical surface within the capillaries as the nickel or cobalt-containing solution flows through the capillaries and delivers nickel or cobalt in solution to the cylindrical growth surface. As the solution flows through the capillary and the wall thickness of the nickel or cobalt tubes increases, the color of the capillary, as viewed from the exterior, changes from silver to reflective nickel or cobalt. Solution can be flowed through the capillary tubes until a desired thickness of the nickel or cobalt microtubes walls is achieved. Eventually, the wall thickness of the hollow microtubes approach the shape of solid wires.

Microstructures Generally

The rate at which material is deposited from the solutions flowed through the capillaries can depend on the reaction temperature of the capillaries and the material flowing through them. For example, relatively high temperature reactions result in relatively rapid deposition rates. This property can be exploited to deposit material selectively at the ends of the capillaries, such that electrically conductive the ends of the capillaries are created, which are electrically isolated from each other. For example, material contained in a solution can be flowed through a capillary at a relatively slow flow rates and at relatively high temperatures, such that material in the solution is deposited very quickly in the first few millimeters of the capillary and is depleted by the time the solution reaches the central portion of the capillary. In this manner, the inner surface of one end of the capillary can be coated with an electrically conductive material. If the process is repeated by flowing solution in the opposite direction through the capillary, the other end of the capillary can be coated. When one or both ends of capillary are coated with an electrically conductive material but the ends are electrically isolated from each other, an electrical potential can be placed between the ends of the capillaries, for example, to apply an electric field to material contained within the capillaries.

The techniques described herein are capable of producing microelectrode arrays containing wires with diameters in the millimeter to sub-nanometer range and with extremely high aspect ratios in a short amount of time (e.g., in less than 12 hours). The size and aspect ratios of the individual wires is limited only by Poiseuille's equation. Additionally, wires fabricated using this process can be mechanically stretched to create nanometer and subnanometer arrays of wires.

The thickness of the deposited electrically conductive metal can be varied by controlling the length of the material in the solutions drawn through the capillaries is exposed to the surface walls. At relatively short deposition times, a thin-walled microtube of electrically conductive metal is deposited on the surface, and at longer deposition times, the thickness of the electrically conductive metal in the capillary tubes approaches the diameter of the capillaries as more material is deposited radially inwardly from the capillary walls.

As a final treatment, the capillaries may be subjected to deposition without flow of the fluid carrying the deposition materials to seal the ends of the structure completely and form electrically conductive metal microwires having hollow cores within the capillaries. Microtube and microwire assemblies and arrays created using the techniques described herein can be used as optically and electrochemically addressable microelectrode arrays with individually resolvable elements.

Structures fabricated using this technique can be liberated from the substrate by selective removal of the substrate material. For example, microtubes, microwires, and microtube and microwire assemblies and arrays fabricated as above could be removed from the substrate, e.g., by selectively etching the substrate away from the microstructures, to give freestanding microtubes, microwires, and microtube and microwire assemblies and arrays.

Applications

Three-dimensional conductive microstructures can be fabricated into conductive microwires and microwire assemblies and arrays for use as microelectrodes and microelectrode assemblies and arrays in the fields of chemistry, biology, and medicine to support a general trend in these fields to manipulate and analyze smaller areas with greater resolution. Microelectrodes are of interest in these fields because electrodes of certain small physical proportions (microelectrodes are generally defined as an electrode with one dimension smaller than 25 μm) exhibit electrochemical behavior that is vastly different than that of a conventional large planar electrode. This different behavior is due to changing mass transport conditions at microelectrodes which results in a rapid steady state response, decreased iR drop, and an increase in the signal to noise ratio. Additionally, their small physical dimensions enable electrochemical stimulation and measurement on much smaller areas than macroelectrodes (e.g., cell groups, individual cells, or structures contained within a cell). Single microelectrodes are of limited use for real-world applications, as their small size generates a small signal which may be easily lost in noise—generally microelectrodes are used for electrochemistry in the confines of a Faraday cage. However, when many microelectrodes are analyzed in parallel as microelectrode assemblies and arrays, they can provide an enhancement in the signal-to-noise ratio that is proportional to the number of elements in the assembly or array.

The physical dimensions of individual microelectrodes and number of microelectrodes in an assembly or array are not the only concerns if one wants to maximize the usefulness of microelectrode assemblies and arrays. To enable electrochemical studies of microscopic regions over large domains or simultaneous electrochemical analysis for multiple analytes, the individual elements in an assembly or array can be individually resolved. Single and multiple microelectrodes fabricated in an assembly or array structure can be used to actively electrochemically interrogate or stimulate an object or sample in the vicinity of the individual microelectrode or microelectrodes at the distal end of the array by applying an electric signal to individual or multiple microelectrodes at the proximal end of the array. Additionally, single and multiple microelectrodes fabricated in an assembly or array structure can be used to passively monitor the electrochemical state of an object or sample at the proximal end of the array.

Microelectrodes fabricated using the techniques described herein can be long slender cylinders having high aspect ratios between their lengths and diameters. As such, this is a distinct advantage over two dimensional microelectrodes and microelectrode arrays that are currently fabricated, as they are not readily usefull with conventional electrochemical instrumentation and cells. The microelectrodes and microelectrode arrays fabricated using the techniques and substrates described herein have the additional advantage of being able to be cleaned using traditional physical polishing techniques. Microelectrodes and microelectrode arrays fabricated using two dimensional techniques must be chemically cleaned. Chemical cleaning often creates a surface on the electrode that is irreproducible for electrochemistry purposes.

Figure 4:
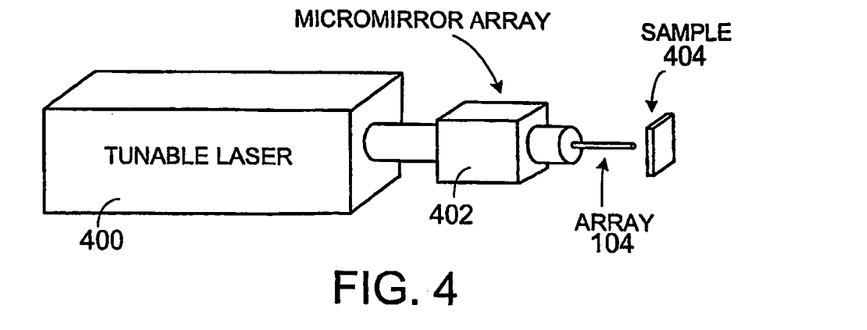
FIG. 4 is a schematic view of an optical system for addressing individual optical fibers of the array shown in FIG. 1.

The new microelectrode arrays are capable of being individually optically and electrochemically addressed. Referring to FIG. 4, individual optical fibers 200 of the array 104 can be addressed by light from a laser 400. Thus, individual parts of a sample 404 can be illuminated or interrogated by the array 104. A mirror array (e.g., Texas Instruments DMD micromirror array device) 402 can be used to selectively couple laser light to particular optical fibers 200 within the array 104. The mirror array is composed of an array of tiltable mirrors in which each mirror can be mechanically controlled to either switch on, with reflection of light, or switch off, with no reflection of light. The laser beam emitted from laser 400 is directed into the micromirror array 402 and illuminates all mirrors in the mirror array. A one-to-one mapping of mirrors in the mirror array to optical fibers 200 of the fiber array 104 exists. Individual mirrors of the micromirror array 202 can be positioned to either direct light into the proximal end of an optical fiber 200 or to direct light away from the fiber. The micromirror array can also be used to direct light received from an optical fiber 200 to a detector (e.g., a CCD detector) that can resolve individual optical fibers 200 within the array 104.

Similarly, individual microelectrodes of the array 104 can be addressed by making electrical connections to individual electrodes of the array 104. A multipotentiostat (e.g., Scribner Associates Inc. Model 900 multichannel microelectrode analyzer) can be used to stimulate and monitor the electrochemical status of the individual microelectrodes. The capillaries in the array 104 can carry both electrical and optical signals, both simultaneously and alternatively. Even when a solid microwire is formed within the capillary, an optical signal can be carried in the core 204 of the optical fiber 200.

The diameters and lengths described in the specific embodiments herein are not at the physical limits of this technique—much narrower, longer, and more irregular features are possible. In addition, it is possible to produce structures composed of materials other than gold and to modify the hollow gold tubes with other chemistries.

The techniques and microelectrodes described herein have a myriad of potential uses. For example, the array 104 can be used as an individually addressable electrode and opto-electrode array for electrochemical and opto-electrochemical analysis and sensing. The array 104 can be used as a surface plasmon resonance sensor for biological sensing of unlabeled biological analytes (e.g., of enzymes, immunoassays, and nucleic acids). The array 104 can used to fabricate ordered electrode arrays for use in basic neuroscience, and more particularly in neuroprostheses and medicine. The array 104 can be used to form materials for use as column packing or electrochemical detectors in chromatographic techniques. The array 104 can be used in array-based high throughput screening techniques or array-based electrochemical synthesis of large numbers of compounds simultaneously, and high-efficiency chemical separations with large arrays of modified microtubes. In addition, the array 104 can be used in the design of integrated circuits using three-dimensional microwires. The array 104 also can be used in the formation of structured high surface area inert materials for catalysis and fuel cell development.

Other Embodiments

It is to be understood that while the invention has been described in conjunction with the detailed description thereof, the foregoing description is intended to illustrate and not limit the scope of the invention, which is defined by the scope of the appended claims and claims that can be added based. Other aspects, advantages, and modifications are within the scope of the following and future claims.

What is claimed is:

1. A method of forming a microscopic structure of a material, the method comprising:
    obtaining a solution comprising the material, wherein the material comprises a metal;
    depositing a bonding layer on an inner wall of a capillary, wherein the capillary has an inner dimension that is smaller than about 300 micrometers;
    establishing a flowing stream of a colloidal suspension of particles within the capillary;
    maintaining the flowing stream of the colloidal suspension of particles until a layer of particles is built up on the bonding layer;
    establishing a flowing stream of the solution in the capillary; and
    maintaining the flowing stream of the solution to deposit material on the layer of particles until a layer of the material is built up along the inner wall of the capillary, thereby forming a microscopic structure.

2. The method of claim 1, further comprising, for each capillary in an assembly of capillaries, wherein each capillary has an inner dimension that is smaller than about 300 micrometers;
    depositing a bonding layer on an inner wall of the capillary;
    establishing a flowing stream of the colloidal suspension of particles within the capillary and maintaining the flowing stream of the colloidal suspension of particles until a layer of particles is built up on the bonding layer; and
    establishing a flowing stream of the solution in the capillary, and maintaining the flowing stream of the solution to deposit material on the layer of particles until a layer of the material is built up along the inner wall of the capillary, thereby forming a microscopic structure.

3. The method of claim 2, wherein the assembly of capillaries is arranged in an array structure.

4. The method of claim 1, wherein the inner dimension is smaller than about 100 microns.

5. The method of claim 1, wherein the inner dimension is smaller than about 10 microns.

6. The method of claim 1, wherein the capillary has a length greater than about 100 microns.

7. The method of claim 1, wherein the capillary has a length of at least about 3 centimeters.

8. The method of claim 1, wherein the bonding layer comprises a bifunctional linker that binds to the inner wall of the capillary at a first end and that binds to material contained in the flowing stream at a second end.

9. The method of claim 1, wherein the bonding layer comprises silane.

10. The method of claim 1, wherein depositing the bonding layer comprises:
    establishing a flowing stream of a solution comprising a bonding material that is deposited on the inner wall of the capillary to form the bonding layer; and
    maintaining the stream until the bonding layer is built up along the inner wall of the capillary.

11. The method of claim 1, wherein the particles are metallic particles.

12. The method of claim 11, wherein the metallic particles are selected from the group consisting of gold colloid particles, silver colloid particles, palladium colloid particles, platinum colloid particles, tin colloid particles, and palladium/tin colloid particles.

13. The method of claim 1, wherein the solution comprising the material comprises a substance that reacts with the layer of particles to deposit the material on the layer of particles.

14. The method of claim 1, wherein the microscopic structure is an electrically conductive structure.

15. The method of claim 1, wherein the metal is selected from the group consisting of copper, nickel, tin, cobalt, platinum, and palladium.

16. The method of claim 1, wherein the material deposited from the flowing stream is gold or silver.

17. The method of claim 1, wherein the capillary is formed within a hollow optical fiber.

18. An apparatus produced by the method of claim 1.

19. A method of forming a microscopic structure of a material, the method comprising:
    obtaining a solution comprising the material, wherein the material comprises a metal;
    establishing a flowing stream of the solution in a capillary, wherein the capillary has an inner dimension that is smaller than about 300 micrometers; and
    maintaining the flowing stream of the solution until a layer is built up along an inner wall of the capillary from material deposited from the flowing stream, thereby forming an electrically conductive microscopic structure.

20. The method of claim 19, further comprising:
    establishing a flowing stream of the solution in an assembly of capillaries, wherein each capillary has an inner dimension that is smaller than about 300 micrometers; and
    maintaining the flowing stream of the solution until a layer is built up along an inner wall of each capillary in the assembly from material deposited from the flowing stream, thereby forming an electrically conductive microscopic structure.

21. The method of claim 20, wherein the assembly of capillaries is arranged in an array structure.

22. The method of claim 19, wherein the inner dimension is smaller than about 100 microns.

23. The method of claim 19, wherein the inner dimension is smaller than about 10 microns.

24. The method of claim 19, wherein the capillary has a length greater than about 100 microns.

25. The method of claim 19, wherein the capillary has a length of at least about 3 centimeters.

26. The method of claim 19, further comprising first depositing a bonding layer on the inner wall of the capillary onto which material from the flowing stream is deposited.

27. The method of claim 26, wherein the bonding layer comprises a bifunctional linker that binds to the inner wall of the capillary at a first end and that binds to material in the flowing stream at a second end.

28. The method of claim 26, wherein the bonding layer comprises silane.

29. The method of claim 26, wherein depositing the bonding layer comprises:
   establishing a flowing stream of a solution comprising a bonding material that is deposited on the inner wall of the capillary to form the bonding layer; and
   maintaining the stream until the bonding layer is built up along the inner wall of the capillary.

30. The method of claim 19, wherein the metal is selected from the group consisting of copper, nickel, tin, cobalt, platinum, and palladium.

31. The method of claim 19, wherein the material deposited from the flowing stream is gold or silver.

32. A method of forming a microscopic structure of a material, the method comprising:
   obtaining a solution comprising the material, wherein the material comprises a metal;
   establishing a flowing stream of the solution in a capillary, wherein the capillary has an inner dimension that is smaller than about 300 micrometers, and wherein the capillary is formed within a hollow optical fiber; and
   maintaining the flowing stream of the solution until a layer is built up along an inner wall of the capillary from material deposited from the flowing stream, thereby forming a microscopic structure.

33. The method of claim 32, further comprising:
   establishing a flowing stream of the solution in an assembly of capillaries, wherein each capillary has an inner dimension that is smaller than about 300 micrometers; and
   maintaining the flowing stream of the solution until a layer is built up along an inner wall of each capillary in the assembly from material deposited from the flowing stream, thereby forming an electrically conductive microscopic structure.

34. The method of claim 32, wherein the inner dimension is smaller than about 100 microns.

35. The method of claim 32, wherein the inner dimension is smaller than about 10 microns.

36. The method of claim 32, wherein the capillary has a length greater than about 100 microns.

37. The method of claim 32, wherein the capillary has a length of at least about 3 centimeters.

38. The method of claim 32, further comprising first depositing a bonding layer on the inner wall of the capillary onto which material from the flowing stream is deposited.

39. The method of claim 38, wherein the bonding layer comprises a bifunctional linker that binds to the inner wall of the capillary at a first end and that binds to material in the flowing stream at a second end.

40. The method of claim 38, wherein the bonding layer comprises silane.

41. The method of claim 38, wherein depositing the bonding layer comprises:
   establishing a flowing stream of a solution comprising a bonding material that is deposited on the inner wall of the capillary to form the bonding layer; and
   maintaining the stream until the bonding layer is built up along the inner wall of the capillary.

42. The method of claim 32, wherein the metal is selected from the group consisting of copper, nickel, tin, cobalt, platinum, and palladium.

43. The method of claim 32, wherein the material deposited from the flowing stream is gold or silver.

44. The method of claim 33, wherein the assembly of capillaries is arranged in an array structure.

* * * * *